United States Patent [19]

Anderson et al.

[11] Patent Number: 4,826,822

[45] Date of Patent: May 2, 1989

[54] LIQUID SUSPENSIONS OF POLYENE ANTIBIOTICS AND USE THEREOF FOR SLIME CONTROL IN INDUSTRIAL WATERS

[75] Inventors: Douglas G. Anderson, Lakeville; Daniel E. Pedersen, Cottage Grove, both of Minn.

[73] Assignee: Ecolab Inc., St. Paul, Minn.

[21] Appl. No.: 854,994

[22] Filed: Apr. 22, 1986

[51] Int. Cl.$^4$ ....................... A61K 47/00; A01N 9/00; B32B 27/40

[52] U.S. Cl. ....................................... 514/31; 536/6.5; 210/764; 435/911

[58] Field of Search .................. 514/31, 515; 435/911; 536/6.1, 6.5; 210/764

[56] References Cited

U.S. PATENT DOCUMENTS

| | | | |
|---|---|---|---|
| 2,797,183 | 6/1957 | Hazen et al. | 167/65 |
| 2,832,719 | 4/1958 | Vandeputte | 167/65 |
| 3,193,448 | 7/1965 | Buckman et al. | 435/911 |
| 3,332,844 | 7/1967 | Vandeputte et al. | 167/65 |
| 3,509,255 | 4/1970 | Mendelsohn | 424/123 |
| 3,517,100 | 6/1970 | Renella | 424/123 |
| 3,517,101 | 6/1970 | Esse | 424/123 |
| 3,549,771 | 12/1970 | Herschler | 435/911 |
| 3,651,218 | 3/1972 | Stolar et al. | 514/31 |
| 3,740,424 | 6/1973 | Vandeputte | 514/31 |
| 3,773,623 | 11/1973 | Hatcher et al. | 435/911 |
| 3,898,343 | 8/1975 | Swered et al. | 514/515 |
| 3,949,086 | 4/1976 | Wolfson | 514/515 |
| 4,148,891 | 4/1979 | Smink | 514/31 |
| 4,185,092 | 1/1980 | Metzger | 424/123 |
| 4,308,375 | 12/1981 | Tang | 536/17 R |
| 4,396,610 | 8/1983 | Witzke | 514/23 |
| 4,707,470 | 11/1987 | Kirsh et al. | 514/31 |

FOREIGN PATENT DOCUMENTS

| | | | |
|---|---|---|---|
| 0888681 | 12/1971 | Canada | 514/515 |

OTHER PUBLICATIONS

Lampen and Arnow, "Significance of Nystatin Uptake for Antifungal Action"; Proceedings of the Experimental Society of Biology and Medicine, vol. 101, pp. 792–797, Jun. 10, 1959.

Rapi, Cocchi, and Belgodere, "Biologifally Active, Water-Soluble Derivatives of Nyatatin"—Chemical Studies: *Chemotherapia,* vol. 6, pp. 326–343 (1963).

*Primary Examiner*—Ronald W. Griffin
*Assistant Examiner*—Nancy S. Carson
*Attorney, Agent, or Firm*—Merchant, Gould, Smith, Edell, Welter & Schmidt

[57] ABSTRACT

A process and composition for controlling slime in industrial waters by the control of slime-forming fungi in the waters. The process comprises the step of adding an effective amount of a polyene antibiotic, such as nystatin, to the waters. The composition is a polyene antibiotic suspension comprising (i) a polyene antibiotic such as nystatin, (ii) a suspension medium such as a glycol, (iii) a sufficient amount of a pH buffer such as an alkali metal phosphate to achieve and maintain the suspension at a pH of about 6–8, (iv) a viscosity modifier such as a heteropolysaccharide, and optionally (v) a surfactant.

39 Claims, 2 Drawing Sheets

LIQUID SUSPENSIONS OF POLYENE ANTIBIOTICS AND USE THEREOF FOR SLIME CONTROL IN INDUSTRIAL WATERS

FIELD OF THE INVENTION

The invention relates to the control of slime through the inhibition of the growth of or the destruction of slime-forming fungi in the industrial waters. More particularly, slime formation is controlled by the intentional addition to industrial waters (e.g. white water in pulp and paper mills) of a fungi controlling amount of a polyene antibiotic, and in particular the addition of the polyene antibiotic nystatin.

BACKGROUND OF THE INVENTION

The formation of slime in industrial waters is a major industrial problem since slime, which is a fungal by-product, can contaminate the end product and can cause equipment malfunction and corrosion.

The term "slime" is a broad one covering a wide range of viscous, mucous, and leathery materials found in industrial waters and on surfaces exposed to these waters. Slimes can be broadly classified as chemical or biological depending upon their cause of formation. Chemical slimes are often the result of an overabundance of a process material, usually an organic polymer, which accumulates both in water and on surfaces. Particulate matter in the water can then adhere to the polymer and may actually form the bulk of the slime mass. This invention relates to biological slimes in which microorganisms bind to surfaces and to each other. Biological slime is the result of the growth of microorganisms. In the paper industry, for example, raw materials and equipment are not sterile and water used in conjunction with such equipment is continuously being contaminated with a wide variety of microorganisms from such sources as wood pulp, chemicals, air, make-up water, and the like. The existing conditions such as temperature and pH permit the growth of microorganisms which can form slime deposits. These slime deposits are typically heterogeneous in composition and routinely contain a significant quantity of microbial cell mass and a variety of particulate material such as wood fiber, clay, pitch and the like.

Many workers have investigated the causes of slime formation in industrial waters and it is generally recognized that a broad spectrum of fungi is responsible for the formation of some slimes, particularly in paper mills that operate under acid conditions.

Historically, slime formation has been controlled by the addition of biocides to industrial waters (e.g. white water associated with the pulp and paper industry). The purpose of these biocides is to destroy or arrest the growth of some of the many organisms present in the water and thereby prevent or retard the formation of slime. Not all known biocides may be used as the biocide must not interfere with the process. Chemicals commonly used as biocides because they do not tend to interfere with the process include a wide variety of thiocyanates, sulfones, phenolics, carbamates, and isothiazolins. However, these materials can be ineffective since they are broad spectrum metabolic poisons that have no particular specificity for fungi and tend to react with bacteria associated with slimes without attacking the causative fungal organisms. In addition, many biocides are toxic to humans and wildlife and can, and often do, adversely affect the environment when the treated industrial water is returned to the environment.

Accordingly, a substantial need exists for an environmentally safe composition which effectively controls the formation of fungal slime in industrial water without interfering with the industrial process and may be used in combination with other slime control means to effectively control all slime in industrial processes.

SUMMARY OF THE INVENTION

Figure 1:
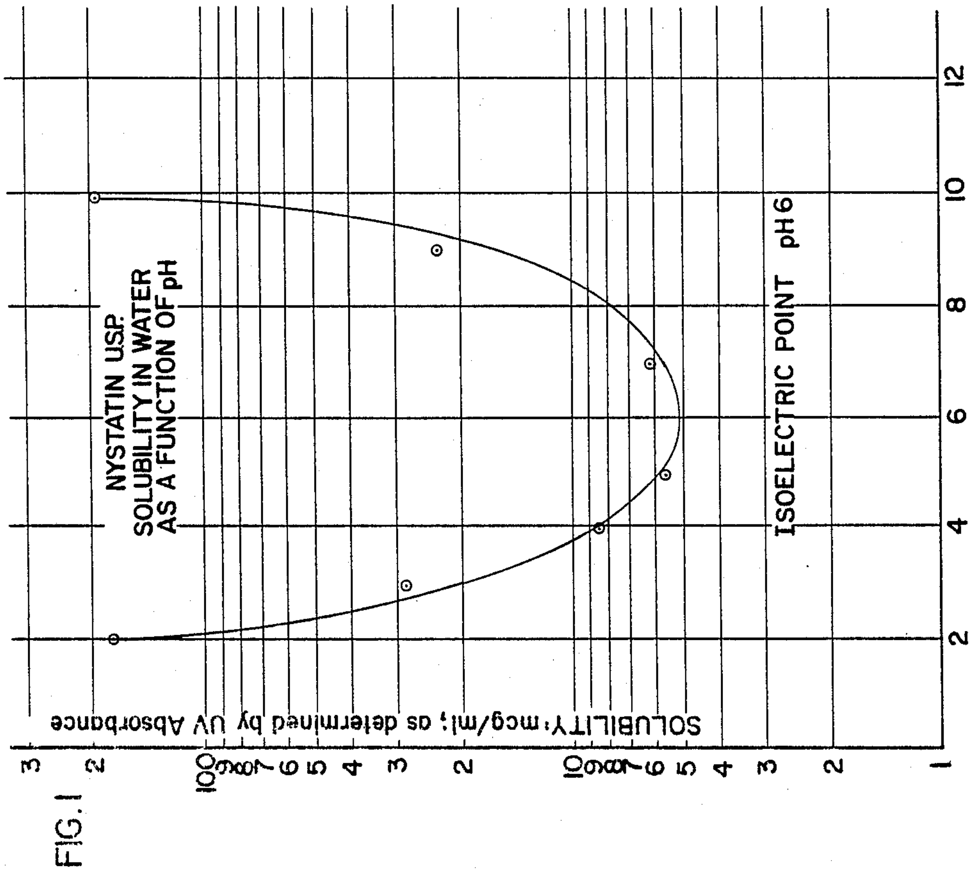
FIG. 1 graphically depicts the relationship of water solubility of nystatin to pH.

We have observed that the addition of a polyene antibiotic (a group of substances known to be highly active specifically against fungi and produced by the Streptomyces genus of microorganisms) and in particular the addition of the polyene antibiotic nystatin, to industrial waters surprisingly controls (e.g. deactivates or kills) slime-forming fungi found within industrial waters and thereby controls or reduces the formation of slime. This result is surprising because nystatin has very low water solubility (about 4 milligrams per milliliter) and is chemically unstable in aqueous solutions, particularly acidic solutions such as are present in pulp and paper mills. Previous use of this antibiotic has primarily been in nonaqueous topical ointments containing high concentrations of nystatin. We have discovered that nystatin can also be an effective fungicide at very low concentrations in an aqueous environment.

The advantages of utilizing a polyene antibiotic to control the formation of slime in industrial water in addition to the fact that it effectively controls slime formation include (i) it does not interfere with the process (e.g. the paper making process) or the product formed thereby (e.g. paper); (ii) it is not toxic to animals ($LD_{50}>8.8$ g/kg); and (iii) it is ecologically safe, as polyene antibiotics are deactivated rather rapidly upon dilution with water and have little or no effect upon organisms other than fungi even when active. The half-life (time to deactivate or destroy ½ of the substance) of polyene antibiotics in water varies greatly with the pH and temperature of the water but generally ranges from about 2 hours to 1 day.

DEFINITIONS

As utilized herein, "suspension medium" refers to a carrier combined with the polyene antibiotic before the latter is added to the industrial water stream. The antibiotic is combined with this carrier to facilitate an even distribution of the polyene antibiotic in the industrial water. Preferred suspension media also create a pumpable product, whereas the polyene antibiotic alone is an umpumpable powder or granular solid. The suspension medium can be any substance in which the polyene antibiotic can be dispersed, and which does not interfere with the practice of the invention.

DETAILED DISCUSSION

Industrial Waters and the Slime Problem

Industrial waters comprise those waters used in industrial plants for such purposes as conveying particulate matter (e.g. paper pulp), cooling and the like. Although the present invention is applicable to a wide range of industrial waters in which slime formation characteristically occurs, we have found that the present invention is particularly useful in the treatment of white water used in pulp and paper mills. Consequently, the present invention will be described with particular reference to the treatment of the industrial waters of paper mill water systems without intending to be limited thereby.

Polyene Antibiotics

Polyene antibiotics constitute a large group of substances produced by the Streptomyces genus of microorganisms. Polyene antibiotics are known fungicides and have been used as fungicides in medicinal ointments and creams.

The task of individually characterizing each member of the group is a difficult one, and of the 60 or 70 such antibiotics which have been given names and which have been examined chemically and biologically only a comparative few have been characterized by full structural elucidation.

Several of the properties common to all polyene antibiotics are (i) they are bound to the mycelium of the culture; (ii) they are quite insoluble in water and the usual organic solvents; and (iii) they are very unstable compounds, being sensitive to acids and alkalis, and decomposed by light and oxygen. Structural features common to all polyene antibiotics are a conjugated polyene chromophore and the presence of a many-membered lactone ring. A general discussion of polyene antibiotics can be found in Kirk-Othmer, *Encyclopedia of Chemical Technology,* 2nd Edition, Vol. 16, pp. 133–412.

The preferred polyene antibiotic to be utilized in the present invention is nystatin. A description and method of producing nystatin is disclosed in U.S. Pat. No. 2,797,183, issued to Hazen et al, which is hereby expressly incorporated by reference.

Nystatin structure $A_1$, which represents the majority of nystatin, is represented by the following formula.

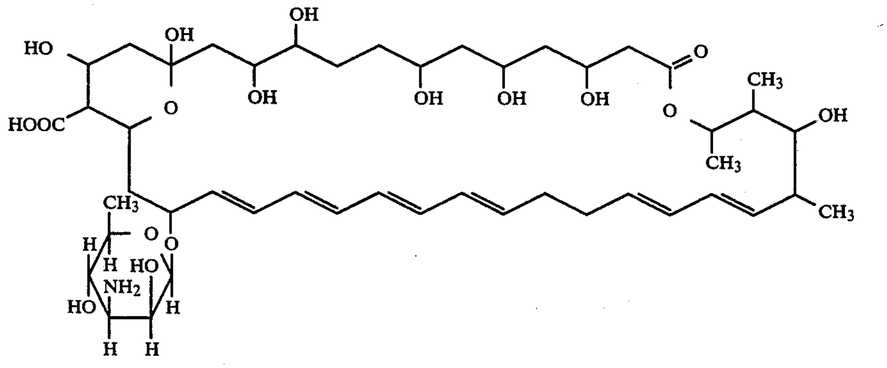

Nystatin also contains a minor amount of nystatin structure $A_2$, which to the best of the inventors' knowledge, has a structure which has not been elucidated.

Since the discovery of nystatin, several procedures have been developed for recovering and purifying nystatin from a Streptomyces culture. Several patents which disclose these processes are Vandeputte, U.S. Pat. No. 2,832,719, Vandeputte et al, U.S. Pat. No. 3,332,844, and Renella, U.S. Pat. No. 3,517,100.

Nystatin, in a form suitable for use in this invention, is commercially available from chemical suppliers including American Cyanamid and Squibb. Nystatin can be purchased in several grades or purities and in several forms. Industrial grade powdered nystatin is suitable for use in this invention although a pure product can of course be used. For reasons of simplicity and ease of handling, Nystatin N.F.I., sold by American Cyanamid, is preferred. This material is a brown granular substance which is hygroscopic and is affected by long exposure to light, heat, and air. The activity of nystatin, and indeed other polyene antibiotics, with respect to their ability to act as fungicides, is typically measured in activity units. American Cyanamid's current production of Nystatin N.F.I. averages about 1700 activity units per milligram.

In this invention a polyene antibiotic is used to control slime formation by the intentional addition of the polyene antibiotic to industrial waters contaminated with fungi. The concentration of the polyene antibiotic can vary widely and will depend upon such factors as the type of industrial water being treated, the conditions of treatment (e.g. temperature and pH of the water), and the particular polyene antibiotic utilized. When using the preferred polyene antibiotic nystatin, concentrations of about 4–60 activity units per milliliter (au/ml) nystatin in the industrial water is generally effective to control slime. For reasons of economics combined with effective slime control, the concentration of nystatin will preferably be in the range of about 6 to 12 au/ml.

Polyene Antibiotic Suspension

In order to insure a thorough dispersion of the polyene antibiotic throughout the industrial water it is advantageous to combine the polyene antibiotic with a suspension medium prior to its addition to the industrial water. Liquid suspension media are preferred because liquids are most convenient for dispensing into the industrial water. Examples of suspension media which may be utilized in the present invention include the glycols such as ethylene and propylene glycol and the polyglycols such as polyethylene glycol and polypropylene glycol. Propylene glycol is the preferred liquid suspension medium because of its viscosity, suspending ability, and water miscibility.

We have also discovered that it is advantageous to add the following compounds to the suspension when a liquid suspension medium is utilized; (1) an effective amount of a pH buffer to maintain the pH of the suspension between about 6.3 to 7.5; and (2) an effective amount of a viscosity modifier to maintain dispersement of the polyene antibiotic in the suspension medium and maintain a pumpable suspension.

Any of the commonly known buffers compatible with the other components may be used, examples of which include inorganic buffers such as potassium and sodium phosphate and organic buffers such as N,N-bis(2-hydroxyethyl)-2-aminoethane-sulfonic acid (BES), bis(2-hydroxyethyl)aminotris(hydroxymethyl) methane (BIS-TRIS), and imidazole. For reasons of economics, sodium phosphate is the preferred pH buffer.

Any of the commonly known viscosity modifiers compatible with the other components may be used, examples of which include heteropolysaccharides such as xanthan gum and KlA112; substituted carboxymethylcelluloses such as carboxymethylcellulose, carboxyethylcellulose, and hydroxyethylcellulose; acrylic gels such as ACRYSOL ICS; amorphous silica such as CABOSIL and LAPONITE; and starch gel. A preferred viscosity modifier, because of ease of formulation is KlA112, an alcohol precipitated, dried and milled microbial polysaccharide made by aerobic fermentation of a carbohydrate with Kelco Isolate S-194, manufactured by KELCO, a division of Merck & Co., Inc.

The amount of viscosity modifier utilized will vary dependent upon the suspension medium used, the polyene antibiotic used, and the particular application of the suspension. In general, good results are obtained if the viscosity of the suspension is about 500 to 3200 cps, or preferably, for reasons of maintaining a good dispersion, ease of pumping and rapid mixing with the water, about 1000 to 3000 cps. This can generally be achieved utilizing about 0.01 to 2%, or preferably, about 0.02 to 0.15% by weight of a suitable viscosity modifier.

In addition, it may be desirable to add an effective amount of surfactant to aid in stabilizing the suspension and improve wetting of the product when it is dispensed into the industrial water. Any of the numerous known surfactants may be employed so long as they are compatible with the other components. Examples of surfactants which may be utilized in the present invention include low foaming nonionic surfactants such as TRITON DF-12 (Rohm & Haas), PLURONIC L-62LF (BASF Wyandotte), and preferably LF-045, a polyoxyethylene, polyoxypropylene glycol sold by Economics Laboratory, Inc.

The surfactant should typically be used at a concentration of about 0.05 to 0.2% by weight.

Effect of pH Upon Properties of Polyene Antibiotic

The pH of the industrial water to which the polyene antibiotic is added has a large impact upon the usefulness of the polyene antibiotic to control the formation of slime in that water. As demonstrated in FIG. 1, the solubility of Nystatin U.S.P. (purified nystatin) is highly dependent upon the pH of the solution, with the solubility of nystatin parabolically increasing with an inflection point at a pH of about 6. Because nystatin is sparingly soluble in water at any pH, a change in the pH of the water effects a large percentage change in the solubility of nystatin (e.g. a change from a pH of 6 to a pH of 4 increases the solubility by 70%).

Figure 2:
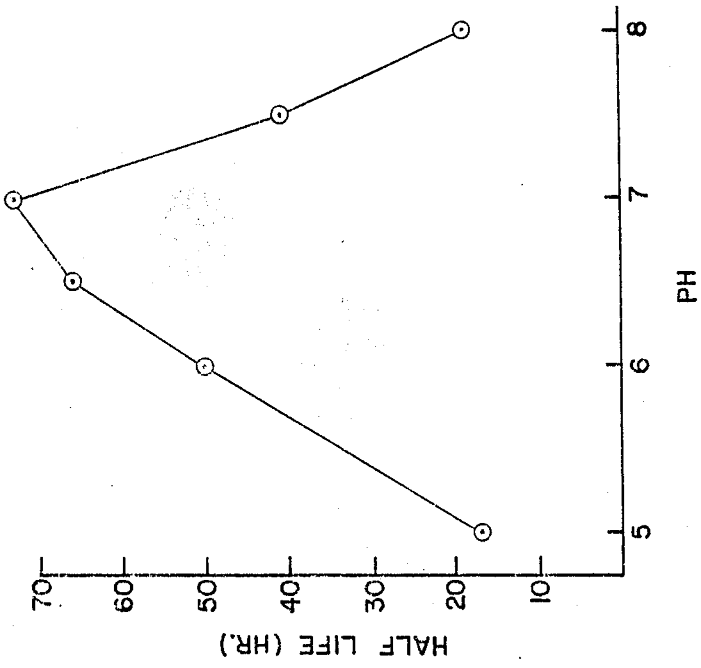
FIG. 2 graphically depicts the relationship of rate of deactivation of nystatin to pH.

As demonstrated in FIG. 2, the stability of nystatin in solution is also highly dependent upon the pH of the solution, with the stablity of nystatin decreasing as the acidity or alkalinity of the solution increases.

By affecting both the solubility and stability of polyene antibiotics, the pH of the industrial water to which they are added strongly impacts the antibiotics' efficacy. As shown in FIG. 1, nystatin is sparingly soluble in water with a noticeable increase in solubility below pH 4 and above pH 8. FIG. 2, however, demonstrates that at such pH extremes, dissolved nystatin becomes significantly less stable, i.e., the half life has declined markedly. Therefore the most effective pH must balance these opposing effects.

We have discovered that nystatin is best able to control slime formation in industrial water when the pH of the water is between a pH of about 4 to 8. Even though the solubility of nystatin is at its lowest in this pH range, we have discovered enough nystatin goes into solution to control the formation of slime and the active half life of the nystatin is long enough to ensure effective slime control. The pH of industrial water utilized in paper mills is generally between about 4.5 to 7.5 which allows the effective use of a polyene antibiotic to control slime formation therein.

Polyene antibiotics have generally been found to be ineffective when the pH of the water to which they are added is less than 2 or greater than 12 as the active half life of the polyene antibiotic is reduced below its effective level.

Placing Polyene Antibiotic in Solution

We believe that in addition to being sparingly soluble and rapidly deactivated in water, polyene antibiotics generally have a slow rate of dissolution in water and are effective against fungi found in an aqueous environment only when in solution. Therefore, polyene antibiotics are most effective in controlling slime formation in industrial water when formulated for rapid dissolution. One of the ways of increasing the rate of dissolution is to increase the surface area of the polyene antibiotic by decreasing particle size. This may be done in a number of ways including mechanical means such as crushing; chemical means such as precipitating the polyene antibiotic from solution and combinations thereof. The preferred method of increasing the surface area of nystatin is to dissolve the nystatin in a highly polar solvent such as N,N-dimethylformamide, remove any undissolved material, and precipitate the nystatin from solution by the addition of a nonsolvent such as water to the solution. The nystatin may then either be separated from the dimethylformamide and water before using or the entire mass of solvent and precipitate may be used.

Use of Polyene Antibiotic to Control Slime Formation

We have discovered that the polyene antibiotic suspension is best formed by first mixing together the suspension medium, the pH buffer, the viscosity modifier and the surfactant when a surfactant is used. The polyene antibiotic is then added to the mixture and thoroughly mixed so that the polyene antibiotic is evenly dispersed to form a suspension. An alternate method for preparing the suspension is to dissolve the polyene antibiotic in a solvent wherein insoluble contaminate material will remain undissolved and can be removed. To the polyene antibiotic solution is then added a mixture of the suspension medium containing; the viscosity modifier, the buffer, and the surfactant, if used.

The suspension may be added to the industrial water in any convenient manner. We have found that a liquid suspension works best because it can be pumped into the industrial water, thereby eliminating the problems associated with dispensing a powdered or granular substance into a liquid.

The suspension may be added to the industrial water at any point where slime control is required. Because we believe that the polyene antibiotic must dissolve to be effective in controlling slime, it is preferable to add the suspension upstream of the point where slime control is desired, but not so far upstream that the polyene antibiotic is deactivated before it reaches the desired point. Because the solubility of the polyene antibiotic is highly dependent upon several variables, in line testing for each process line is recommended to determine how far upstream the polyene antibiotic should be added.

The following specific Examples, which include the best mode, were prepared and tested as described.

EXAMPLE I

In a two thousand milliliter beaker equipped with a 3.25 inch, 6 vane turbine impeller mounted on a standard laboratory overhead mixer, 1.125 grams of $Na_2HPO_4$ was dissolved in 335 grams of water. After the dissolution was complete 0.225 g of xanthan gum, a viscosity modifier, was dispersed, under high agitation, into the mixture. After all solids were dissolved, 787.5 g propylene glycol and 1.5 g LF-045, a polyoxyethylene, polyoxypropylene glycol, were added, under high agitation, to the mixture. 375 g of −10 to +50 mesh powdered Nystatin N.F.I. was then added to the mixture, the mixture was agitated until all nystatin particles were thoroughly wetted. The suspension was then processed (homogenized) with a TEKMAR pilot scale bench top homogenizer until the mixture reached a smooth homogeneous consistency (all particles sized less than about 40 mesh). The resultant composition comprised:

| | | |
|---|---|---|
| Suspension Medium | Propylene glycol | 52.5 wt % |
| Suspension Medium | Deionized water | 22.31 wt % |
| Polyene Antiobitic | Nystatin N.F.I. | 25.0 wt % |
| Surfactant | LF-045 | 0.10 wt % |
| pH Buffer | $Na_2HPO_4$ | 0.075 wt % |
| Viscosity Modifier | Xanthan gum | 0.015 wt % |

EXAMPLE II 0.075 g $Na_2HPO_4$, as a pH buffer, was dissolved in 22.41 g deionized water in a 250 ml beaker agitated by a 1.5 inch diameter two blade turbine impeller mounted on a standard laboratory overhead mixer. 0.015 g xanthan gum, as a viscosity modifier, was then dispersed, under high agitation, into the mixture. 52.5 g propylene glycol was then added, under high agitation, to the mixture. 25.0 g powdered (≦50 mesh) Nystatin was then added to the mixture which was agitated for about 30 minutes to form a homogeneous suspension. The nystatin was powdered prior to being added to the mixture by grinding in a Keisch laboratory grinder having a 0.5 mm screen; separating the ground nystatin with a standard ASTM #50 screen (openings of 0.0117 inches); and regrinding the nystatin which failed to pass through the #50 screen. The resultant composition comprised about:

| | | |
|---|---|---|
| Suspension Medium | Propylene glycol | 52.5 wt % |
| Suspension Medium | Deionized $H_2O$ | 22.41 wt % |
| Polyene Antibiotic | Nystatin N.F.I. (powdered) | 25.0 wt % |
| pH Buffer | $Na_2HPO_4$ | 0.075 wt % |
| Viscosity Modifier | Xanthan gum | 0.015 wt % |

EXAMPLE III 42.8 g Nystatin N.F.I. powdered in accordance with the process disclosed in Example II was mixed with 100 g dimethylformamide and agitated for approximately 30 minutes. The solution/suspension was then fitered through #4 Whatman paper under vacuum and the filter cake formed washed with an additional 35 g of dimethylformamide. The total dissolved nystatin solution obtained was about 105 g.

Separately, in a 250 ml. beaker 0.075 g $Na_2HPO_4$ was dissolved in 28.325 g deionized water. 0.1 g (KlA112), as a viscosity modifier, was then added to the mixture and agitated until completely dissolved. The pH of the mixture was then adjusted to about 6.3 using a lN HCl solution. The mixture was slowly added to about 43.0 g of the nystatin solution under constant agitation. 28.5 g of propylene glycol was then added to the mixture and the mixture agitated until a stable suspension was formed. The resulting composition had a pH of about 6.3 and comprised about:

| | | |
|---|---|---|
| Suspension Medium | Nystatin N.F.I. solution in dimethylformamide | 43 wt % |
| Suspension Medium | Propylene glycol | 28.5 wt % |
| Suspension Medium | Deionized water | 28.325 wt % |
| pH Buffer | $Na_2HPO_4$ | 0.075 wt % |
| Viscosity Modifier | K1A112 | 0.1 wt % |

Example II demonstrates a process for increasing nystatin solubility by mechanically producing smaller particles of Nystatin. Example III increases nystatin solubility by removing impurities to which nystatin binds and producing smaller particles by dissolving nystatin and discarding the undissolved impurities.

EXAMPLE IV

A suspension made in accordance with Example II is formed comprising:

| | | |
|---|---|---|
| Suspension Medium | Propylene glycol | 50 wt % |
| Suspension Medium | Deionized water | 29.85 wt % |
| Polyene Antibiotic | Nystatin N.F.I. | 20 wt % |
| pH Buffer | $Na_2HPO_4$ | 0.05 wt % |
| Viscosity Modifier | Xanthan gum | 0.10 wt % |

EXAMPLE V

A suspension made in accordance with Example III is formed comprising:

| | | |
|---|---|---|
| Suspension Medium | Example II Nystatin N.F.I. solution in dimethylformamide | 5 wt % |
| Suspensium Medium | Propylene glycol | 80 wt % |
| Suspension Medium | Deionized water | 14.85 wt % |
| pH Buffer | $Na_2HPO_4$ | 0.10 wt % |
| Viscosity Modifier | K1A112 | 0.05 wt % |

EXAMPLE VI

A single celled fungus, *Saccharomyces cerevisiae* (ATCC #2601) was grown for 18 hours on 1/10 x Difco Sabouraud Dextrose Broth at 30° C. The cells were then diluted with the broth to an ATP concentration of $6.2\times10^{-9}$ g/ml. The ATP levels were determined using a photometer and protocol manufactured by Turner Designs.

0.01 grams purified Nystatin U.S.P. (5910 activity units/mg) was dissolved in 0.5 ml dimethylformamide. After complete dissolution of the nystatin 9.5 ml of water was added to the solution and a nystatin precipitate formed. The mixture of dimethylformamide, water and nystatin was agitated to ensure a homogeneous mixture and enough of the mixture was added to the fungus culture to achieve a level of 12 activity units nystatin/ml.

Figure 3:
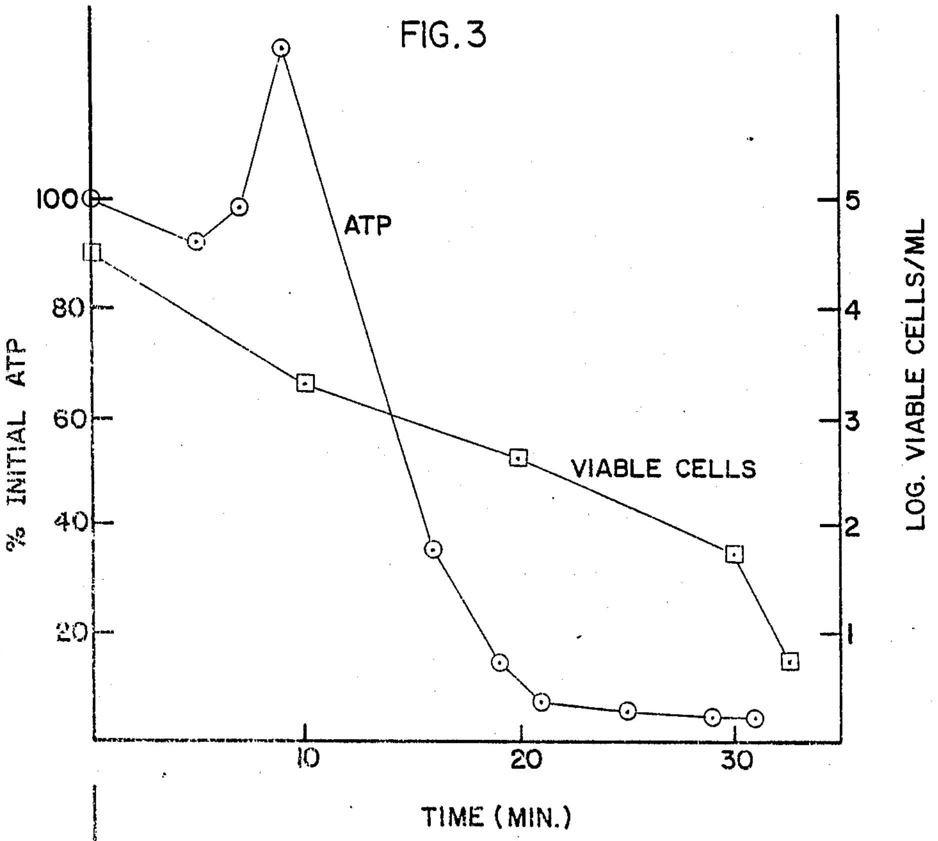
FIG. 3 graphically depicts the relative change in amount of ATP and viable fungal cells in a fungal growth medium after the addition of nystatin to the culture.

As shown in FIG. 3 the ATP level initially increased slightly and then dropped to 4% of the initial level. The viable cells also dropped dramatically from $2\times10^4$ cells/ml to 5 cells/ml demonstrating that nystatin is fungicidal and acts quickly, and that the level of ATP generally corresponds to the number of viable cells, indicating that the monitoring of ATP level can accurately depict the effect of nystatin upon fungi. The enumeration of viable cells at a given time was determined by diluting a sample of the fungal cells in 0.3 mM $KH_2PO_4$ buffered water. The diluted solution comprised one part fungal cells per 100 parts buffer water. Aliquots of 10 ml, 1 ml and 0.1 ml of the diluted solution were placed in sterile polystyrene petri dishes. Approximately 20 ml of molten agar medium sold under the trademark ANTIBIOTIC 12 by Difco was added to the diluted solution in the petri dishes. The petri dishes were incubated at 30° C. for two days and the number of resultant colonies counted. Each colony was assumed to represent one surviving viable cell in the original experiment.

EXAMPLE VII

Figure 4:
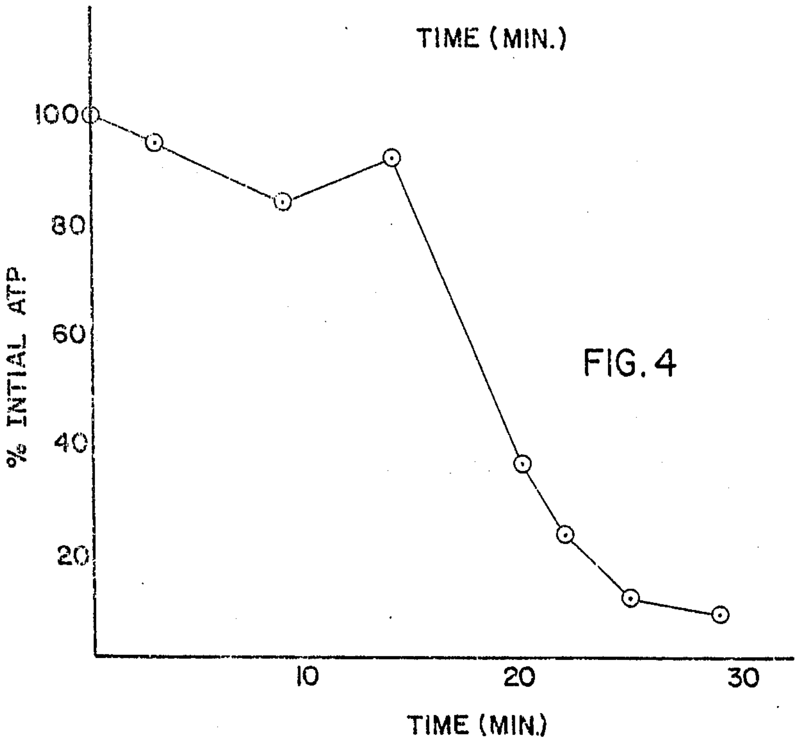
FIG. 4 graphically depicts the relative change in amount of ATP in a fungal growth medium after the addition of a nystatin suspension to the culture.

A culture of Saccharomyces cervisiae fungus was grown and diluted in accordance with the procedure of Example VI to an ATP concentration of $1.4\times10^{-8}$ g/ml. At time zero a sufficient amount of a nystatin suspension prepared in accordance with Example I is added to the fungus growth to achieve a level of 18 activity units nystatin/ml. As shown in FIG. 4 the ATP levels dropped sharply during the period of 15–25 minutes after addition of the suspension to the fungus growth indicating that the suspension will effectively kill fungi.

EXAMPLE VIII

Approximately 40 lbs. of a suspension, formed in accordance with the procedure or Example I, is added over a 30-minute period to the water stream of a paper mill operating at a fiber concentration of about 0.8% and having an output of 300 tons of paper per day. The suspension is added immediately upstream of the primary fan to keep the screens, cleaners and headbox free of fungal slime.

The foregoing Examples and discussion provide the detailed discussion of the preferred embodiments of the invention. Since many embodiments of the invention can be made without departing from the spirit and scope of the invention, the invention resides in the claims hereinafter appended.

I claim:

1. A process for controlling fungi in industrial water which comprises the step of adding an effective fungi controlling amount of a polyene antibiotic to the water.

2. The rpocess of claim 1 wherein the polyene antibiotic is nystatin.

3. The process of claim 2 wherein about 4 to 60 activity units of nystatin are added per milliliter of industrial water.

4. The process of claim 2 wherein about 6 to 12 activity units of nystatin are added per mililiter industrial water.

5. The process of claim 1 wherein the polyene antibiotic is added in the form of a liquid suspension.

6. The process of claim 5 wherein the liquid suspension comprises the polyene antibiotic suspended in a substantailly inert suspension medium.

7. The process of claim 6 wherein the suspension further comprises an amount of pH buffer sufficient to maintain the pH of the suspension between about 6 to 8.

8. The process of claim 6 wherein the suspension further comprises an amount of viscosity modifier sufficient to maintain a stable dispersion of the polylene antibiotic throughout the suspension.

9. The process of claim 6 wherein the polyene antibiotic comprises nystatin and the suspension medium comprises an alkylene glycol.

10. The process of claim 7 wherein the polylene antibiotic comprises nystatin and the pH buffer comprises a phosphate buffer.

11. The process of claim 8 wherein the polyene antibiotic comprises nystatin and the viscosity modifier comprises a heteropolysaccharide.

12. A process for controlling fungi in industrial water which comprises the step of adding an effective fungi controlling amount of a liquid suspension to the water; the liquid suspension comprising:
(a) a polyene antibiotic;
(b) a substantially inert suspension medium;
(c) an amount of a pH buffer sufficient to maintain the pH of the suspension between about 6 to 8; and
(d) an amount of a viscosity modifier sufficient to increase the viscosity of the suspension to about 500–3,200 cp.

13. The process of claim 12 wherein the polyene antibiotic comprises nystatin which is present in the industrial water at a concentration of about 4 to 60 activity units nystatin per milliliter of industrial water.

14. The process of claim 12 wherein the polyene antibiotic comprises nystatin which is present in the industrial water at a concentration of about 6 to 12 activity units nystastin per milliliter of industrial water.

15. A process for controlling or reducing the amount of fungi in industrial water comprising the steps of:
(a) forming a liquid suspension comprising:
(i) nystatin,
(ii) a liquid suspension medium,
(iii) a pH buffer in an amount sufficient to maintain the pH of the suspension between about 6 to 8;
(iv) a viscosity modifier in an amount sufficient to increase the viscosity of the suspension to about 1,000 to 3,000 cp, and;
(b) adding into the industrial water a sufficient amount of the liquid suspension to achieve a concentration of about 6 to 12 activity units of nystatin per mililiter of industrial water.

16. The process of claim 15 wherein the liquid suspension further comprises about 0.05–0.2 wt-%, based upon the suspension, surfactant.

17. The process of claim 16 wherein (i) the suspension medium comprises propylene glycol; (ii) the pH buffer comprises an alkali metal phosphate; and (iii) the surfactant comprises a polyoxyethylene, polyoxypropylene glycol.

18. The process of claim 15 wherein (i) the suspension medium comprises propylene glycol; (ii) the pH buffer comprises an alkali metal phosphate; and (iii) the viscosity modifier comprises a heteropolysaccharide.

19. The process of claim 18 wherein the suspension comprises:

(a) about 3 to 25 wt-% nystatin;
(b) about 5 to 30 wt-% propylene glycol;
(c) about 0.05 to 0.2 wt-% alkali metal phosphate; and
(d) about 0.02 to 0.2 wt-% heteropolysaccharide.

20. The process of claim 16 wherein the suspension comprises:

(a) about 3 to 25 wt-% nystatin;
(b) about 5 to 30 wt-% propylene glycol;
(c) about 0.05 to 0.2 wt-% alkali metal phosphate;
(d) about 0.02 to 0.2 wt-% heteropolysaccharide; and
(e) about 0.05 to 0.2 wt-% polyoxyethylene, polyoxypropylene glycol.

21. A liquid suspension for contorlling fungi in industrial water which comprises:

(a) a polyene antibiotic;
(b) a suspension medium;
(c) an amount of a pH buffer sufficient to maintain the pH of the suspension between about 6 to 8;
(d) an amount of a viscosity modifier sufficient to increase the viscosity of the suspension to about 500–3,200 cp.

22. A suspension as recited in claim 21 further comprising about 0.05–0.2 wt-% based upon the suspension, surfactant.

23. A suspension as recited in claim 21 wherein the polyene antibiotic comprises nystatin.

24. A suspension as recited in claim 22 wherein the polyene antibiotic comprises nystatin.

25. A suspension as recited in claim 23 wherein the suspension medium comprises a glycol.

26. A suspension as recited in claim 23 wherein the suspension medium comprises propylene glycol.

27. A suspension as recited in claim 24 wherein the suspension medium comprises propylene glycol.

28. A suspension as recited in claim 21 wherein the pH buffer comprises an alkali metal phosphate.

29. A suspension as recited in claim 21 wherein the viscosity modifier comprises a heteropolysaccharide.

30. A suspension as recited in claim 22 wherein the surfactant comprises polyoxyethylene, polyoxypropylene glycol.

31. A suspension as recited in claim 23 wherein the suspension comprises about 3 to about 25 wt-% nystatin.

32. A suspension as recited in claim 24 wherein the suspension comprises about 3 to about 25 wt-% nystatin.

33. A suspension as recited in claim 23 wherein the suspension comprises:

(a) about 3 to 25 wt-% nystatin;
(b) about 5 to 30 wt-% glycol;
(c) about 0.05 to 0.2 wt-% of an alkali metal phosphate; and
(d) about 0.05 to about 0.2 wt-% of polyoxyetylene, polyoxypropylene glycol.

34. A suspension as recited in claim 24 wherein the suspension comprises:

(a) about 3 to 25 wt-% nystatin;
(b) about 5 to 30 wt-% glycol;
(c) about 0.05 to 0.2 wt-% of an alkali metal phosphate;
(d) about 0.02 to 0.2 wt-% heteropolysaccharide; and
(e) about 0.05 to about 0.2 wt-% polyoxyethylene, polyoxypropylene glycol.

35. A suspension as recited in claim 23 wherein the suspension comprises:

(a) about 3 to 25 wt-% nystatin;
(b) about 5 to 30 wt-% glycol;
(c) about 0.05 to 0.2 wt-% of an alkali metal phoshate;
(d) about 0.02 to 0.2 wt-% heteropolysaccharide; and
(e) about 0.05 to about 0.2 wt-% polyoxyethylene, polyoxypropylene glycol.

36. A process for controlling fungi in white water employed in the manufacture of paper which comprises the step of adding an effective fungi controlling amount of a polyene antibiotic to the water.

37. The process of claim 36 wherein the polyene antibiotic is selected from the group consisting of nystatin, nystatin salts and mixtures thereof.

38. A process for controlling fungi in pulp and paper white water which comprises the step of adding an effective fungi controlling amount of a liquid suspension to the water; the liquid suspension comprising:

(a) a polyene antibiotic;
(b) a substantially inert suspension medium;
(c) an amount of a pH buffer sufficient to maintain the pH of the suspension between about 6 to 8; and
(d) an amount of a viscosity modifier sufficient to increase the viscosity of the suspension to about 500 to 3,200 cp.

39. The process of claim 38 the antibiotic comprises nystatin, the suspension mediuim comprises propylene glycol, the pH buffer comprises an alkali metal phospahte, the viscosit modifier comprises a heteropolysaccaride and the suspension comprises:

(a) about 3 to 25 wt-% nystatin;
(b) about 5 to 30 wt-% propylene glycol;
(c) about 0.05 to 0.2 wt-% alkali metal phosphate; and
(d) about 0.02 to 0.2 wt-% heteropolysaccardie

* * * * *

UNITED STATES PATENT AND TRADEMARK OFFICE

CERTIFICATE OF CORRECTION

PATENT NO. : 4,826,822

DATED : May 2, 1989

INVENTOR(S) : DOUGLAS G. ANDERSON et al

It is certified that error appears in the above-identified patent and that said Letters Patent is hereby corrected as shown below:

Column 7, line 41, for "Antiobitic" read --Antibiotic--.
Column 8, line 12, for "fitered" read --filtered--.
Column 9, line 56, for "or Example" read --of Example--.
Column 10, line 5, for "rpocess" read --process-.
Column 10, line 11, for "mililiter" read --milliliter--.
Column 10, line 17, for "substantailly" read --substantially--.
Column 10, line 24, for "polylene" read --polyene--.
Column 10, line 29, for "polylene" read --polyene--.
Column 10, line 53, for "nystastin" read --nystatin--.
Column 10, line 68, for "mililiter" read --milliliter--.
Column 11, line 29, for "contorlling" read --controlling--.
Column 12, line 13, for "polyoxyetylene" read --polyoxyethylene--.

UNITED STATES PATENT AND TRADEMARK OFFICE
CERTIFICATE OF CORRECTION

PATENT NO. : 4,826,822

DATED : May 2, 1989

INVENTOR(S) : DOUGLAS G. ANDERSON et al

It is certified that error appears in the above-identified patent and that said Letters Patent is hereby corrected as shown below:

Column 12, line 50, for "38 the" read --38 wherein the--.
Column 12, line 51, for "mediuim" read --medium--.
Column 12, lines 52-53, for "phospahte" read --phosphate--.
Column 12, line 53, for "viscosit" read --viscosity--.
Column 12, line 59, for "heteropolysacchardie" read --heteropolysaccharide--.

Signed and Sealed this

Sixteenth Day of January, 1990

*Attest:*

JEFFREY M. SAMUELS

*Attesting Officer* | *Acting Commissioner of Patents and Trademarks*